US008705833B2

(12) United States Patent
Yagi et al.

(10) Patent No.: US 8,705,833 B2
(45) Date of Patent: Apr. 22, 2014

(54) COMPUTER-AIDED STAINING OF MULTISPECTRAL IMAGES

(75) Inventors: Yukako Yagi, Boston, MA (US); Pinky A. Bautista, Arlington, MA (US)

(73) Assignee: The General Hospital CorporationMA (US)

( * ) Notice: Subject to any disclaimer, the term of this patent is extended or adjusted under 35 U.S.C. 154(b) by 142 days.

(21) Appl. No.: 13/093,122

(22) Filed: Apr. 25, 2011

(65) Prior Publication Data
US 2012/0269417 A1    Oct. 25, 2012

(51) Int. Cl.
*G06K 9/00*  (2006.01)
(52) U.S. Cl.
USPC ............................................. 382/133; 702/19
(58) Field of Classification Search
None
See application file for complete search history.

(56) References Cited

U.S. PATENT DOCUMENTS

| 2004/0093166 | A1* | 5/2004 | Kil | 702/19 |
| 2010/0075373 | A1 | 3/2010 | Hoyt | |
| 2010/0195903 | A1 | 8/2010 | Tani | |
| 2012/0269417 | A1* | 10/2012 | Bautista et al. | 382/133 |
| 2013/0071002 | A1* | 3/2013 | Otsuka et al. | 382/133 |

FOREIGN PATENT DOCUMENTS

WO    2010017822 A1    2/2010

OTHER PUBLICATIONS

Bautista, Pinky A., et al. "Digital staining for multispectral images of pathological tissue specimens based on combined classification of spectral transmittance." Computerized Medical Imaging and Graphics 29.8 (2005): 649-657.*
Gilbertson, John R., et al. "Primary histologic diagnosis using automated whole slide imaging: a validation study." BMC clinical pathology 6.1 (2006): 4.*
Bautista, Pinky A., et al. "Digital staining of unstained pathological tissue samples through spectral transmittance classification." Optical review 12.1 (2005): 7-14.*
Bautista, Pinky A., et al.: "Multispectral Image Enhancement for H&E Stained Pathological Tissue Specimens", Proc. of SPIE, vol. 6918, pp. 691836-1-691836-11 (2008).
Bautista, Pinky A., et al.: "Digital Staining of Unstained Pathological Tissue Samples through Spectral Transmittance Classification", Optical Review, vol. 12 No. 1 pp. 1-8 (2005).
Bautista, Pinky A., et al.: "Digital staining for multispectral images of pathological tissue specimens based on combined classification of spectral transmittance", Computerized Medical Imaging and Graphics, vol. 29, pp. 649-657 (2009).
Masanori Mitsui, et al.: "Color Enhancement in Multispectral Image Using the Karhunen-Loeve Transform", Optical Review vol. 12, No. 2, pp. 69-75 (2005).
Masahiro Yamaguchi, et al.: "Color image reproduction based on the multispectral and multiprimary imaging: Experimental evaluation", Proc. of SPIE, vol. 4663, pp. 15-26 (2002).
William J. Cukierski, et al.: "Moving Beyond Color: The Case for Multispectral Imaging in Brightfield Pathology", 2009 IEEE ISBI, pp. 1111-1114.

(Continued)

*Primary Examiner* — Tahmina Ansari
(74) *Attorney, Agent, or Firm* — Quarles & Brady LLP; Yakov Sidorin

(57) ABSTRACT

A system and method for digital staining of an image of biological tissue acquired with the use of multispectral imaging system. The method includes spectral enhancement of the originally-acquired image, which results in differentiation of colorimetrically-similar components of the tissue, and a linear mapping of the spectrally-enhanced image to an estimated target image that represents the spectral response of the tissue manually stained with a target stain.

25 Claims, 6 Drawing Sheets

(56) References Cited

OTHER PUBLICATIONS

William J. Cukierski, et al.: "Metamerism in Multispectral Imaging of Histopathology Specimens", 2010 IEEE ISBI, pp. 145-148.

PCT International Search Report and Written Opinion, PCT/US2012/034762, Jul. 19, 2012.

* cited by examiner

COMPUTER-AIDED STAINING OF MULTISPECTRAL IMAGES

TECHNICAL FIELD

The present invention relates to evaluation and analysis of histological structures and, in particular, to revealing the morphology of these structures by digitally emulating the effects produced by staining the histological structures with dyes.

BACKGROUND ART

Abnormal or diseased biological tissues are often diagnosed and monitored with histopathology. For example, a majority of cancer cases are diagnosed by histopathological assessment of a biopsy sample. The presence, concentration and distribution of biological molecules (such as nucleic acid, protein or lipids for example) or different portions and structures of the tissue can be determined by selecting a specific combination of chemical stains and fixatives. Visualization of the histological structures in a biological tissue sample is a basic procedure undertaken by a pathologist to reach a specific diagnosis on the disease that might have afflicted a patient, for example, kidney disease, liver disease, and the like. In particular, a pathologist assesses any variation in the morphological structures of the different components of the tissue, such as irregularities in shapes and sizes, and correlates the identified changes, if any, to a particular disease. Normally, a pathologist uses a physically stained tissue sample (a sample stained with a dye, for example) and relies on color cues to interpret texture and morphology of such tissue in arriving at his diagnosis. In comparison with an unstained tissue sample, in which histological structures are not clearly differentiated, and which generally appears colorless when viewed under a microscope, a stained tissue specimen provides a clear illustration of the histological structures as well as vivid visual discrimination of the different tissue components. Various types of dyes are available to stain the tissue samples, each of the dyes labeling the histological structures with distinguishing colors, thereby emphasizing the differences among such components. Choice of which type of stain to use depends on mainly on what tissue structure is to be assessed in the diagnosis. Popular for routine staining are, for example, the Hematoxylin and Eosin (H&E) dyes that facilitate differentiation between the nuclear region and the cytoplasm and connective tissues. A well-trained histopathologist can diagnose and grade the severity of a tissue disease based on colour, shape, degree of staining and pattern of a variety of stains.

More recently, digital technology has been developed to digitally "stain" images. Digital staining of an image is understood as the process of digitally converting the original image into an image with visual characteristics mimicking those that would be observed if the tissue were to be conventionally stained. As is the case with many traditional clinical applications being advanced with digital technology, the advantages of digital staining are multifold. For example, digital staining provides a quantitative result, which could aid diagnosis and reduce the hands-on time of a trained histopathologist as well as reduce intra-histologist variation in diagnosis. It offers the opportunity to develop a variety of digital staining procedures and has the potential to be significantly cheaper than existing chemical staining techniques. Moreover, digital staining does not destroy the biological sample and therefore the same sample could be analyzed by multiple digital staining protocols. Finally, the digital staining process does not involve toxic chemical stains, and is, therefore, intrinsically harmless to the user.

Of course, in the sense that implementations of digital staining are designed to mimic or reflect visual characteristics provided to the clinician when performing traditional staining, the clinical utility and, ultimately, clinical acceptance of digital staining systems and methods are predicated on the accuracy of this mimicking of traditional staining visualizations. For example, one method of digital image staining relies on spectral classification of tissues and often cannot delineate portions of a given image representing tissues with similar spectral attributes. In particular, the reliable quantitative differentiation between those components of unstained tissue that have similar spectral response to a conventional physical staining (referred to herein as colorimetrically-similar components) cannot be assured with the use of conventional digital staining. Thus, the field of digital staining continues to develop with the goal of improving clinical feasibility of such digital staining techniques.

It is desired, therefore, to provide apparatus and method capable of improving the accuracy of digital staining techniques in reflecting traditional staining results, such as, for example, by resolving similarities is spectral response and appropriately enhancing histopathological images produced through digital staining for visualization by the user.

SUMMARY OF THE INVENTION

The present invention overcomes the abovementioned drawbacks by providing a system and method for imaging a biological tissue.

In one embodiment, an apparatus of the invention includes an input, configured to receive at least one of imaging data acquired from a tissue sample and an image of that tissue sample, and a computer processor configured to enhance spectral signals associated with the received imaging data and/or image and to linearly transform the enhanced spectral signals based on estimated transmission data and training data, thereby generating a representation of a reaction of the biological tissue to a target chemical stain. The image of the biological tissue may include a multispectral image representing a plurality of spectrally-discrete images acquired in a plurality of discrete spectral bands. At least one of the estimated transmission data and training data may related to and/or depend on such target chemical stain. The reaction of the biological tissues to a target chemical stain may include a chance of an optical characteristic of the tissue, for example a change of the transmission spectrum. An apparatus may further include a display, electrically connected to the processor, that is adapted to present for visual evaluation at least one of the image of the biological tissue, an enhanced image corresponding to the enhanced spectral signals, and the representation of a reaction of the tissue to a target chemical stain. In a specific embodiment, the visual representation of a reaction is made in an RGB color space.

Embodiments of the invention further provide for an apparatus for imaging a biological sample that includes (i) an optical system having an input configured to receive light from the sample, (ii) an output connected to the input along at least one optical axis, (iii) a spectrally-selective system disposed along at least one such optical axis and adapted to process the received light in a plurality of discrete spectral bandwidths to form a corresponding plurality of image-forming signals, and (iv) an optical detector that receives the plurality of image-forming signals and forms a corresponding plurality of images therefrom. In addition, the apparatus may further include a processor programmed to receive an image from the plurality of images and spectrally enhance such received image to produce an enhanced images and to further transform the enhanced image into a target image representing a reaction that the biological sample would exhibit if it were exposed to a target chemical stain. The apparatus may further include a display configured to display a visually-perceivable representation of the target image illustrating an expected reaction of the biological sample to the target chemical stain.

In a specific embodiment, a processor of the embodiment may be programmed to implement a digital filter system that is configured to receive at least one image formed on the detector, and digitally transform image-forming data of the received image such as to form a target image based on estimated transmission data and training data. The digital filter system may include a multiplier element configured to linearly scale the image-forming data that has been changed by an amount dependent on the average spectral transmittance of a background image. In a specific embodiment, where the biological sample includes tissue components that are substantially visually indistinguishable, the digital transformation causes the target image to include the tissue components color-coded so as to be visually discernable. For example, the processor may be further programmed to digitally transform image-forming data such as to create an enhanced image differentiating between the tissue components otherwise have colorimetrically-similar characteristics. The image differentiation may be based on appropriate color-coding representing an expected reaction of the biological sample when such sample is stained with a target chemical stain. The display is configured to present a visually-perceivable target image demonstrating this reaction of the sample to a target chemical stain. A target image may further include the enhanced image that has been linearly transformed based on a matrix product of a pseudo-inversed matrix containing the estimated transmission data and a matrix containing the target image transmission data.

Embodiments of the invention further provide a method for digital staining of a histopathology image. The method includes receiving an image of a tissue sample, which contains colorimetrically-similar tissue components, to acquire original spectral transmission data representing the tissue sample and modifying the original spectral transmission data based on at least one of a reference spectral transmission data and a modulation factor such as to derive enhanced spectral transmission data representing differences between the colorimetrically-similar tissue components. The method may further include mapping the enhanced spectral transmission data into a target spectral transmission data that represents a spectral response of the tissue sample to a target stain. The method may further include at least one of converting said target spectral transmission data into an RGB color space and presenting an image corresponding to so converted target spectral transmission data for visualization. In one embodiment, receiving an image of a tissue may includes receiving an image in which colorimetrically-similar tissue components cannot be visually distinguished, and modification of the original spectral transmission data includes modification based on transmission parameters that are dependent on a spectral characteristic of a background image. The process of mapping of the enhanced spectral transmission data may include a linear transformation of these data performed based on tissue classification that has been defined with respect to the target stain.

Embodiments of the invention additionally provide a computer program product for use on a computer system that assigns color-codes to colorimetrically-similar components of a biological tissue. The computer program product includes a tangible computer-usable storage medium having computer-readable program code thereon, and the computer readable program code, in turn, includes at least a program code for deriving such image parameters of at least the colorimetrically-similar components of the biological tissue that are visually indistinguishable. In addition, the computer program product may include program code for color-coding of the derived image parameters. Such color-coding may be based on reference image data, enhanced image data, and training data and result in formation of a target image that represents a reaction of the biological tissue to a target chemical stain In such target image, however, the colorimetrically-similar components appear to be visually discernable. In a specific implementation the color-codes may be assigned based on coefficients representing linear relationship between the enhanced image data and the target image. The computer-readable program code may further include program code for storing a plurality of image data sets (representing at least the colorimetrically-similar components in a plurality of discrete spectral bands) on the tangible computer-readable storage medium.

Additionally, embodiments of the invention provide a system for image analysis including an imaging device adapted to generate at least one image of an object that includes image acquisition parameters representing colorimetrically-similar components of the object; and a calibration device that receives at least one image generated by the imaging device and changes at least one image acquisition parameter of that image based on a comparison between the image acquisition parameters of the image and an estimated set of image acquisition parameters that the colorimetrically-similar components of the object would acquire if they were exposed to a target chemical reaction. The target chemical reaction may include staining the colorimetrically-similar components of the object with a target dye. Changing of at least one image acquisition parameter may be carried out based on a combination of considerations including the image acquisition parameter itself, a reference spectral transmission data obtained in the process of generating the image at hand, and a linear scaling factor. In a specific embodiment, the linear scaling factor may, in turn, depend on an estimated image acquisition parameter representing a response of colorimetrically-similar components to a target chemical reaction. The calibration device of the system may include a computer processor programmed to derive at least one image acquisition parameter from an image generated by the imaging device, which may be configured to produce images of an object in discrete spectral bands.

BRIEF DESCRIPTION OF THE DRAWINGS

The invention will be more fully understood by referring to the following Detailed Description in conjunction with the Drawings.

DETAILED DESCRIPTION OF SPECIFIC EMBODIMENTS

Figure 1A:
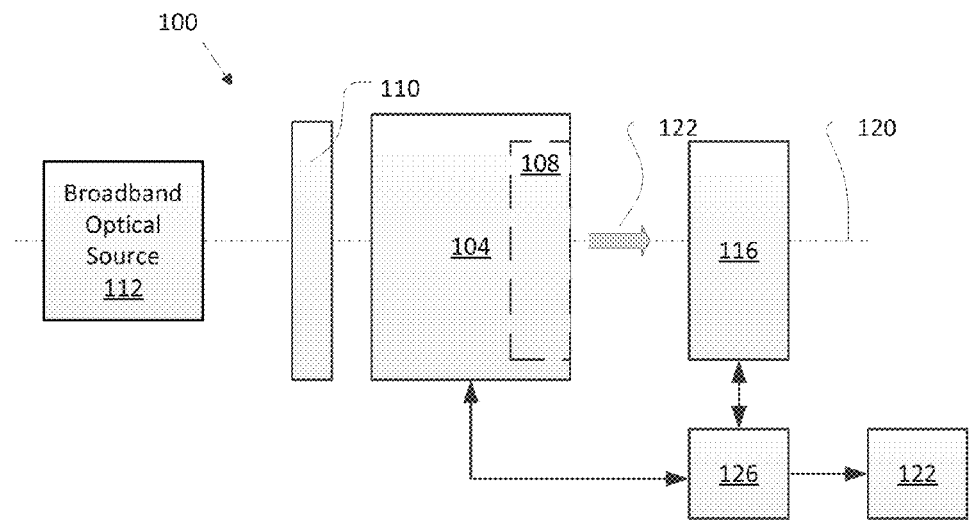
FIGS. 1A and 1B schematically illustrate examples of multispectral imaging (MSI) systems in accordance with the present invention.

For the purpose of the description and appended claims, the identified terms are defined as follows, unless the context otherwise requires.

The term "image" generally refers to an ordered representation of detector output corresponding to spatial positions. For example, a visual image may be formed, in response to a pattern of light detected with an optical detector, on a display device X such as a video screen or printer.

The term "digital staining" generally refers to emulating the effect of conventional physical staining of the biological tissue by subjecting an image of the tissue to a transformation through algorithmic processes. In other words, digital staining implies the application of digital processing techniques to transform one image of a sample to another image that represents the sample stained with a particular stain.

Generally, the terms "original image" and "original image data" refer to the initial image and corresponding image data used in a discussed chain of image transformation. An original image may be an image of stained or unstained tissue acquired with the use of an MSI system. In comparison, the "target image" and a corresponding "target image data" refer to the image of the tissue that has been physically stained with the target stain and corresponding image data, respectively.

The following specification provides a description of the embodiments of the invention with reference to the accompanying drawings. In the drawings, wherever possible, the same reference numerals and labels refer to the same or like components or elements. It will be understood, however, that similar components or elements may also be referred to with different numerals and labels.

Throughout this specification, a reference to "one embodiment," "an embodiment," or similar language implies that a particular feature, structure, or characteristic described in connection with the embodiment referred to is included in at least one embodiment of the present invention. Thus, phrases "in one embodiment," "in an embodiment," and similar terms used throughout this specification may, but do not necessarily, all refer to the same embodiment. Moreover, it will be understood that features, elements, components, structures, details, or characteristics of various embodiments of the invention described in the specification may be combined in any suitable manner in one or more embodiments. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention.

The schematic flow chart diagram that is included is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The general framework of a conventional digital stating methodology includes the identification of the different tissue components in an unstained tissue sample, the classification of these components, and the visualization of these components as pseudo-stained components as an image, such as in the red-green-blue (RGB) color space. While the use of conventional quantitative algorithms that implement digital staining reduces the resulting errors from sample to sample, their remaining deficiency is the inability to quantitatively and reliably differentiate between those components of unstained tissue that have similar spectral responses to conventional physical staining. Components of unstained tissue that have similar spectral responses to conventional physical staining are referred to herein as colorimetrically-similar components. An example of colorimetrically-similar tissue components is provided by collagen fiber and smooth muscle. In accordance with the present invention, methods and apparatus are disclosed for digital processing of images of a biological tissue that allows reliable quantitative identification and classification of colorimetrically-similar tissue components and a visualization of these components. For example, the invention may be employed with a multispectral imaging (MSI) system.

MSI equips the analysis of pathology specimens with computerized microscope-based imaging systems by providing access to spectral distribution of an image at a pixel level. While there exists a variety of multispectral imaging systems, an operational aspect that is common to all of these systems is a capability to form a multispectral image. A multispectral image is one that captures image data at specific wavelengths or at specific spectral bandwidths across the electromagnetic spectrum. These wavelengths may be singled out by optical filters or by the use of other instruments capable of selecting a pre-determined spectral component including electromagnetic radiation at wavelengths beyond the range of visible light range, such as, for example, infrared (IR). In comparison with panchromatic imaging, the plurality of color channels of a standard MSI system typically represents only a small subspace of the available spectral data.

Figure 1B:
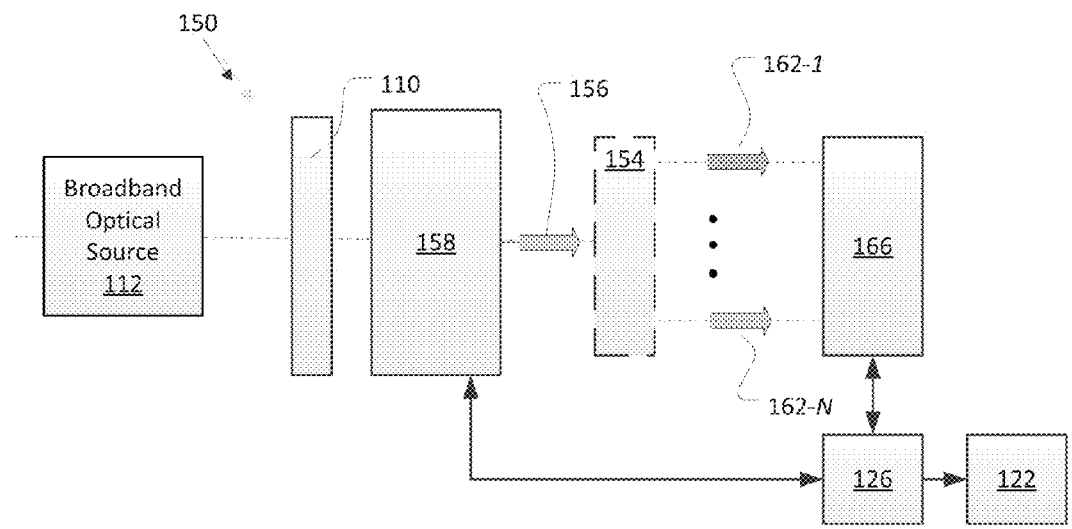

Two common types of an MSI system facilitating the acquisition of images of unstained tissue are schematically illustrated in FIGS. 1A and 1B. FIG. 1A shows an apparatus 100 including an optical imaging system 104, a portion 108 of which contains a spectrally-selective system that is tunable to define a pre-determined number N of discrete optical bands. The optical system 104 is adapted to image a tissue sample 110, illuminated in transmission with a broadband light source 112 onto an optical detector 116. As shown, the optical imaging system 104, which in one embodiment may include a magnifying system such as, for example, a microscope, has a single optical axis 120 generally spatially aligned with a single optical output 122 of the optical system 104. The system 104 forms a sequence of images of the tissue 110 as the spectrally-selective system 108 is being adjusted or tuned (for example with a computer processor 126) such as to assure that images are acquired in different discrete spectral bands. The apparatus 100 may additionally contain a display 122 in which appears at least one visually-perceivable image of the tissue from the sequence of acquired images. The spectrally-selective system 108 may include an optically-dispersive element such as a diffractive grating, a collection of optical filters such as thin-film interference filters or any other system adapted to select, in response to either a user input or a command of the pre-programmed processor 126, a particular pass-band from the spectrum of light transmitted from the light source 112 through the sample 110 towards the detector 116.

An alternative implementation 150 of an apparatus adapted to simultaneously take a multiplicity of spectrally-discrete optical images in several spectral bands is shown in FIG. 1B. Here, the spectrally-selective system 154 defines several optical outputs corresponding to N discrete spectral bands. The system 154 intakes the transmitted light output 156 from the optical system 158 and spatially redirects at least a portion of this light output along N spatially different optical paths 162-1 through 162-N in such a way as to image the sample 110 in an identified spectral band onto a detector system 166 along an optical path corresponding to this identified spectral band. It is appreciated that another alternative embodiment (not shown) may combine features of the embodiments 100 and 150.

Example of Image Acquisition.

Figure 1C:
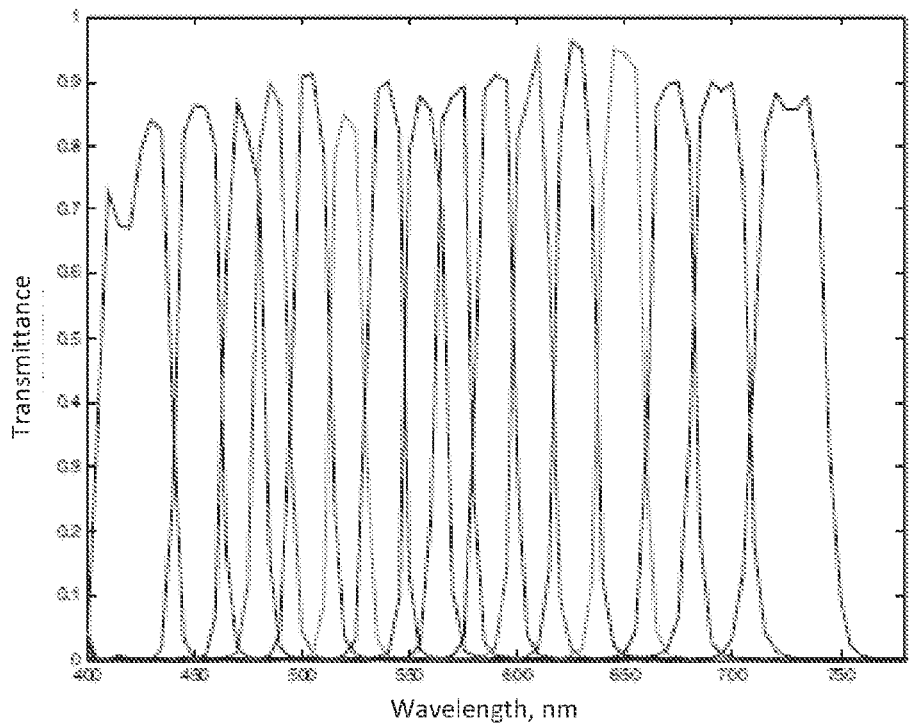
FIG. 1C presents an optical spectrum of a spectrally-selective system of an MSI used in accordance with the present invention.

In further reference to FIG. 1A, multispectral images of biological samples were captured with a magnifying imaging system 104 such as an Olympus BX-62 optical microscope. The magnifying imaging system was equipped with a rotatable spectrally-selective system 108 including N narrow-band interference filters that, at discretion of a user, could be sequentially or out-of order disposed across an optical axis of the microscope. Each of the interference filters was characterized by a corresponding transmission bandwidth. Light 122, that has passed from the sample 110 through the microscope 104 and a chosen interference filter 108 towards the optical detector 116, formed an image on the detector in a corresponding spectral band. A combination of N images collected at N spectral bands could be either appropriately combined to form a multi-spectral image of a sample or analyzed separately. In one specific embodiment, the rotatable spectrally-selective filter system included $N_1$=16 filters, each filter defining an individual spectral channel the spectral responses of which, aggregately spanning the visible spectrum region, are shown in FIG. 1C. In another specific embodiment, the multispectral image data was acquired in $N_2$=55 spectral bands.

A 2000×2000 pixel CCD camera and the microscope were controlled by a computer processor 126 programmed to operate a video-grabbing electronic circuitry and further adapted to store the acquired images on a computer-readable tangible storage medium for future processing. It is appreciated that, generally, a different number of spectral channels may be employed in an MSI of choice and a possible extension of the filter spectral range to the near infrared (NIR) portion of the spectrum is within the scope of the invention. The processor 126 was further programmed to enable interactive selection of the histologic components of the imaged sample. In particular, an image sub-set corresponding to a particular pixel or a group of pixels could be selected for storage, analysis and visualization on the display 122.

Examples of Digital Staining Procedure.

The invention utilizes a transformation of the acquired multispectral image of the tissue, which transformation may, sequentially, spectrally enhance the original transmission spectrum of an optical image of the tissue and then transform the enhanced spectral transmission data into a target image. The purpose of spectral enhancement (or spectral enhancement mapping) is to produce an enhanced transmission spectrum of the original image that is sufficient to reliably differentiate between conventionally colorimetrically-indistinguishable tissue components and to derive a measure of such differentiation. The spectral enhancement may be accomplished with the use of principal component analysis (PCA), which is a multivariate data-analysis algorithm adapted to reduce the dimensionality of the data set while preserving as much as possible the information contained in that data set. As a result of spectral enhancement mapping, therefore, the original data set may be mapped into a set of enhanced image data set through a process of scaling that is dependent on differences between the transmission spectrum of the original image and that estimated with the dominant principal component vectors. The purpose of transforming is to convert the enhanced image data into the target transmission image spectrum with the use of matrix theory. In contradistinction to the related art, in doing so the algorithm of the invention further uses the enhanced image data, for example, instead of an original, unmodified image of the tissue, as input for the target transformation process. The matrix-based transformation may include a linear transformation between the enhanced and target image data sets. The present invention may additionally include a "visualization" mapping of the obtained target transmission spectrum into corresponding data that can be presented to a viewer in a visually-discernable fashion (for example, as an RGB image on a monitor display).

Figure 2:
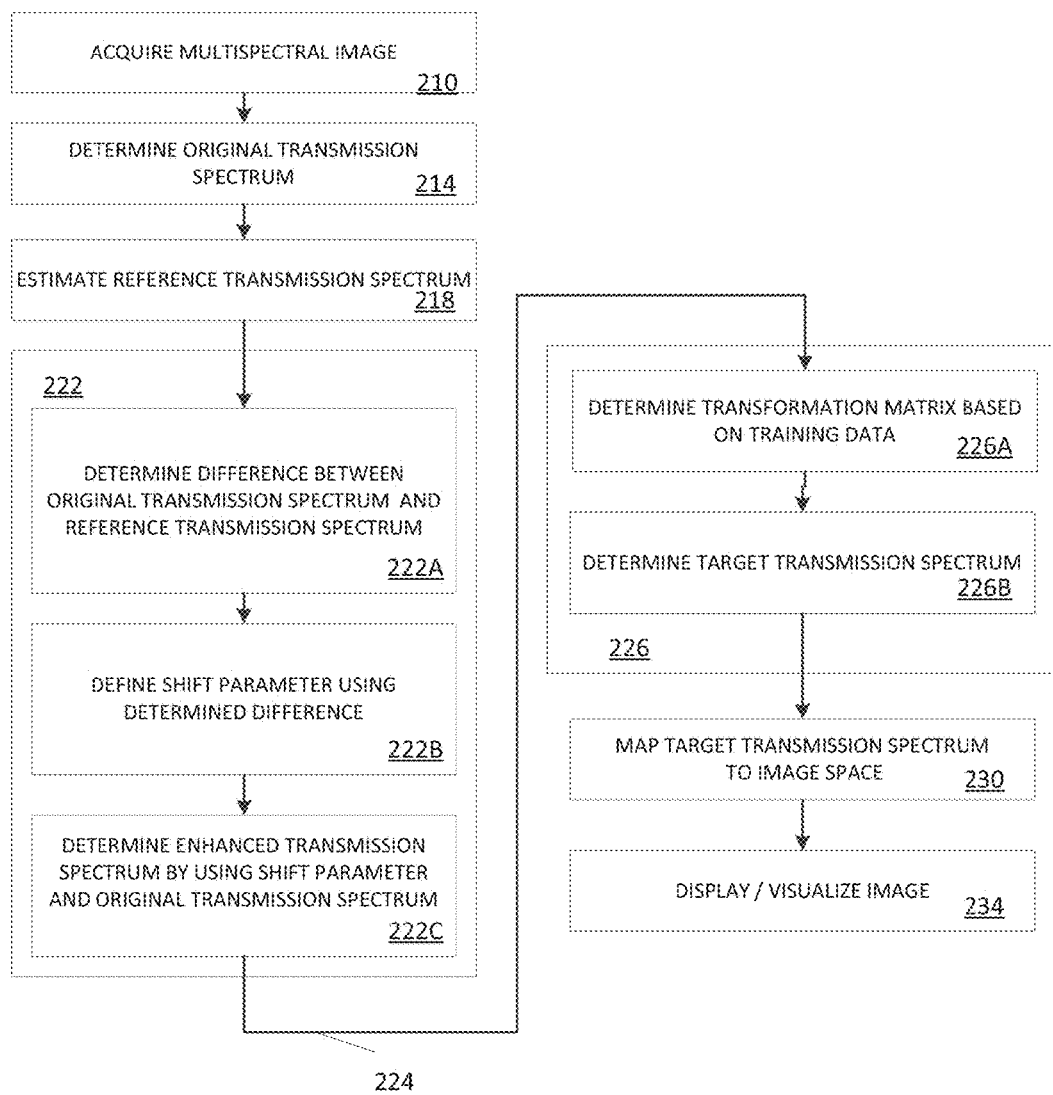
FIG. 2 is a flow-chart setting forth steps of a digital-staining process in accordance with the present invention.

Referring now to FIG. 2, a flow-chart setting forth the exemplary steps for a digital staining procedure in accordance with the present invention is illustrated. The original image data, acquired, for example, with the use of an MSI system at step 210, is used to extract, at step 214, information characterizing transmittance of the tissue sample in each of the N spectral bands, on a pixel-by-pixel basis. A transmittance value of a given image pixel located at coordinates (x, y) of an image and in a spectral band with a central wavelength λ is calculated as:

$$t_o(x, y, \lambda) = \frac{I_0(x, y, \lambda) - I_{d0}(x, y, \lambda)}{I_{ref}(x, y, \lambda) - I_{dref}(x, y, \lambda)}. \tag{1}$$

Here, $I_0$ and $I_{ref}$ are the intensity value of the original image and that of the background image. $I_{d0}$ and $I_{dref}$ represent, respectively, the dark-current detector readings for the object and background images. The background image may be acquired, for example, by imaging a scene against which the tissue is being imaged, for example by imaging a slide with no tissue sample on it. The dark-current image may be obtained with no illumination of the detector. The pixel transmittance value is calculated, therefore, as the ratio of the sample's and background (for example, sample holder) grey-level signals.

The reference vector t'(r) containing transmittance data with the use of PCA is estimated, at step 218, with the use of PCA with m-dominant principal component (PC) vectors according to:

$$t'(r) = \sum_{i=1}^{m} \alpha_i v_i + \bar{t} \quad (2),$$

where the location r of the pixel is appropriately defined though the coordinates (x, y), and $\alpha_i$ and $v_i$ are the ith PC coefficient and PC vector, respectively. The element $\bar{t}$ denotes the spectral transmission vector of those image portions that are not intended to be enhanced and generally corresponds to the averaged spectral transmittance of the background image. The PC vectors may be derived based on the spectral transmittance of the background image.

The original spectral transmission of an N-band image pixel, acquired at step 214, is further modified in a spectral enhancement procedure 222 according to:

$$t_e(r) = W[t_o(r) - t'(r)] + t_o(r) \quad (3),$$

to define the enhanced transmission spectrum $t_e(r)$ of the pixel, where t'(r) is the reference spectral transmission N×1 vector estimated with PCA at step 218, and W corresponds to the N×N weighting matrix the elements of which operate as modulation factors to the original spectral transmission N×1 vector $t_o(r)$ shifted by the reference N×1 vector t'(r). The spectral enhancement procedure 222 includes determining, at step 222A, the difference between the original spectral transmission vector and the reference spectral transmission vector; ascertaining of the shift parameter, at step 222B, based on the determined difference and the weighting matrix W; and defining the enhanced spectral transmission vector by the appropriate shifting of the original spectrum vector, at step 222C.

Figure 3A:
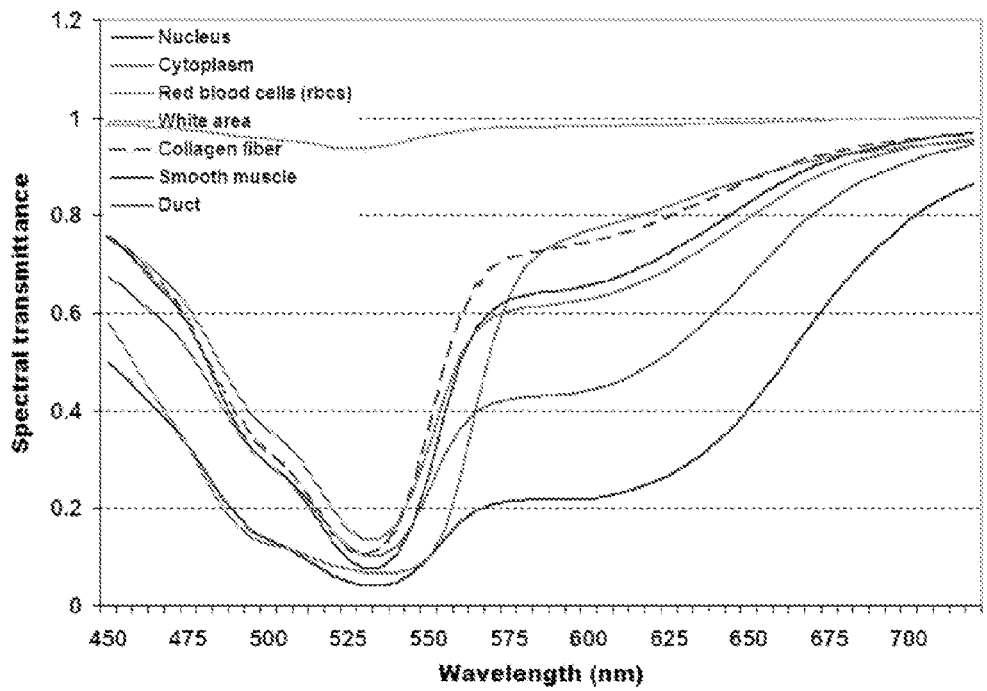
FIGS. 3A and 3B are graphs illustrating spectral transmission characteristics of various tissue components ascertained, in accordance with the present invention, from an original image of the tissue and from a spectrally-enhanced image, respectively.
Figure 3B:
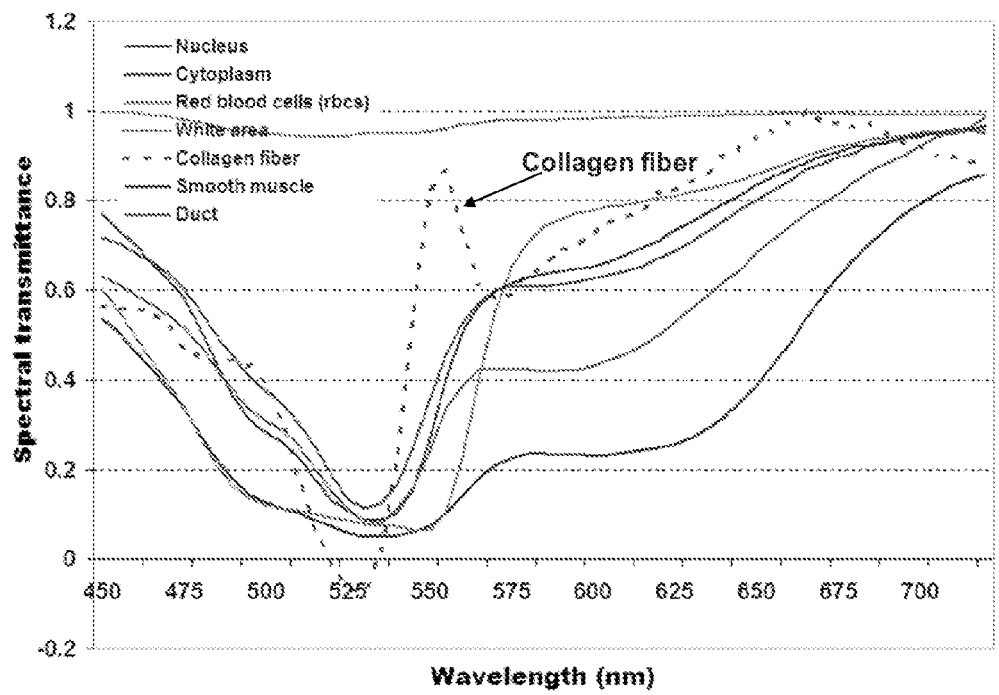

FIGS. 3A and 3B are graphs that illustrate some advantageous features of a spectral image enhancement in accordance with the present invention as applied to the liver tissue images acquired with the use of the MSI system described above. FIG. 3A represents the original transmittance spectra of the different H&E stained tissue components, while FIG. 3B shows the corresponding enhanced spectra. The purpose of this experiment was to delineate the collagen finer from the remaining tissue. Denoting $T_{HE}$ to be the matrix containing the H&E spectral transmittance data of all components of the tissue and $T'_{HE}$ to be a matrix containing the H&E spectral transmission data of all components except for the collagen fiber, the average spectral transmission $\bar{t}$ was ascertained from $T'_{HE}$. The reference spectral transmission was estimated with the use of 5 PC vectors. The spectral enhancement procedure was performed according to Equation (3), with the weighting matrix W determined as $$[W]_{ij} = \begin{cases} k, & i = j \\ 0, & i \neq j, \end{cases} \quad (4)$$

with k=10. The enhanced difference between the spectral configuration of the collagen fiber and the remaining tissue can be clearly appreciated from FIGS. 3A, 3B by comparing the dotted line corresponding to the collagen fiber spectrum and other graphs representing spectra of difference components. In a related embodiment, the design of the weighting matrix W can be extended by, for example. assigning non-zero values to the off-diagonal elements of the matrix.

In further reference to FIG. 2, the enhanced spectral transmission image data 224 are further mapped, 226, to their target spectral configuration. The transformation matrix used in the mapping procedure 226 is derived, at step 226A, from the training data stored in the system. In a particular case, where the mapping of the enhanced spectral transmission data set $t_e$ to the estimated target spectral transmission data set $t_{target}$ that corresponds to $t_0$ is assumed to be linear, the N×N transformation matrix Q is defined as a least-mean-square solution of the equation:

$$Q = T_e^+ T_{target} \quad (5),$$

that describes the dependence between the pre-determined training image data sets $T_e$ and $T_{target}$. Here, $T^+_e$ is the pseudo-inverse of $T_e$. The enhanced spectral transmission data is further converted, at step 226B, to the target spectral transmission data according to:

$$t_{target} = t_e Q \quad (6).$$

In a specific embodiment of the invention, a linear transformation procedure 226 was carried out to map the transmission spectra representing the enhanced H&E image of the tissue, which included both the smooth muscle and the collagen fiber, to a corresponding Masson's trichrome (MT) stained image. In this case, the transformation matrix was derived as:

$$Q = T_e^+ T_{MT} \quad (5a).$$

The linearity of transformation (6) relies on the assumption that the spectral samples stored in the training data set correspond to the tissue regions that are spectrally separated from one another, particularly in the data representing the original image, and that the structural and biochemical composition of tissue components determines how a given tissue component responds to a given stain. For example, the nuclear regions of the tissue may exhibit color variations that depend on the presence of chromatin structures, while the color variation of the cytoplasm will depend on the presence of a protein. A red blood cell generally assumes pink coloration and is stained lighter towards the center due to its biconcave shape. The white region is devoid of any tissue structures and, as a result, generally does not generate any spectral response to either hematoxylin or eosin dye. The training data of the related art are empirically predetermined, therefore, by imaging tissue components in a number of tissue classes such as nucleus, cytoplasm, red blood cells, and the white region and judiciously classifying the acquired images in accordance with spectral responses of a particular component to a pre-determined type of physical stain. For illustrations of schemes conventionally used in tissue classification and identification, the reader is referred to, for example, *Comp. Med. Imaging and Graphics*, 29, 649-657 (2005); or *Optical Review*, 12, 1-8 (2005). Related art adapted the use of "tissue classification" that included characteristics of histopathological tissue images of multiple classes of tissue by employing training data that represent enhanced transmission spectra for a variety of unstained tissue components as well as target transmission spectra for a variety of tissue components stained with different stains. As a result, the conventionally used algorithms utilizing such classification are bound not only to utilize multiple transformation matrices to effectuate a linear transformation procedure that would be similar to that of step 226 of the embodiment 200, but be limited to distinguishing the tissue components having spectra that do not overlap or at least are easily spectrally separable. In contradistinction, the embodiment of the present invention may reduce or substantially eliminate the need for multi-element spectral classification since only one transformation matrix is required and does not require that the original spectra of the tissue components chosen to be enhanced do not overlap. In fact, embodiments of the present invention allow for augmentation and differentiation of the spectra that not only overlap but are very similar (i.e., the spectra of colorimetrically-similar tissue components).

Examples of Visualization of the Digitally Stained Multispectral Image.

It is appreciated that, at the output of the step 226B, the embodiment 200 produces a target image that can be described by the chromaticity coordinates X, Y, and Z of the color space formulated by the Commission Internationale de l'Eclairage's (CIE) and summarized in its 1931/1964 standards. This target image may include a combination of the plurality of images acquired, in different spectral bands, with the MSI system. The technology of color is relatively complex, but a fairly comprehensive discussion is given by F. W. Billmeyer and M. Saltzman in *Principles of Color Technology*, $2^{nd}$ Edition, J. Wiley and Sons Inc. (1981). To facilitate the visual perception and conventional description of an image in the RGB-color space, and referring to FIG. 2 yet again, an embodiment of the digital staining algorithm may further include a visualization step 230 and a display step 234, at which the N-band linearly transformed transmittance spectrum 226B is further converted to its equivalent RGB color values. Such transformation can be carried out according to, for example:

$$\begin{bmatrix} \alpha_R \\ \alpha_G \\ \alpha_B \end{bmatrix} = \begin{bmatrix} X_R & X_G & X_B \\ Y_R & Y_G & Y_B \\ Z_R & Z_G & Z_B \end{bmatrix}^{-1} \left( \begin{bmatrix} X \\ Y \\ Z \end{bmatrix} - \begin{bmatrix} X_{black} \\ Y_{black} \\ Z_{black} \end{bmatrix} \right), \quad (7)$$

where $$X = \int_{\lambda_1}^{\lambda_2} \bar{x}(\lambda) t_{target}(\lambda) d\lambda \quad (8a)$$

$$Y = \int_{\lambda_1}^{\lambda_2} \bar{y}(\lambda) t_{target}(\lambda) d\lambda \quad (8b)$$

$$Z = \int_{\lambda_1}^{\lambda_2} \bar{z}(\lambda) t_{target}(\lambda) d\lambda \quad (8c)$$

and where $\bar{x}(\lambda), \bar{y}(\lambda), \bar{z}(\lambda)$ denote the CIE XYZ color matching functions; $E(\lambda)$ denotes the spectrum of light illuminating the tissue sample; $X_i, Y_i, Z_i$, i=R, G, B, are the XYZ chromaticity coordinates of the RGB primary colors; and $X_{black}, Y_{black}, Z_{black}$ are the XYZ chromaticity coordinates of the background of the monitor in which the final RGB image characterized by its $\alpha_R, \alpha_G, \alpha_B$ color values can be displayed. In one embodiment, $\lambda_1$=450 nm and $\lambda_2$=720 nm.

As another example, FIGS. 4A, 4B, 4C, and 4D illustrate operability of the embodiment 200 of the invention applied to an input multispectral image that was acquired in $N_2$=55 bands. In particular, FIG. 4A is an original H&E stained image of the tissue, FIG. 4B is an image of manually stained MT image, FIG. 4C is an enhanced H&E stained image, and FIG. 4D is a digitally-produced MT stained version of the image of FIG. 4A. The original input image was spectrally enhanced according to (3) and further linearly re-mapped according to (6), where the transformation matrix Q was derived according to (5a). For visualization purposes, both the linearly mapped (linearly transformed) transmission spectrum and the enhanced transmission spectrum were independently converted to the RGB color values according to (7) and (8a, 8b, 8c). The five (5) PC vectors derived from $T_{HE}'$ were used to estimate the spectral transmittance of the multispectral pixels, and the diagonal elements of the weighting factor matrix W were set to k=5. FIGS. 4A-4D show the manually stained H&E and Masson's trichrome (MT) stained images, and the results of the spectral enhancement and digital staining. The magnified portions of the images of FIGS. 4A-4D are shown in FIGS. 5A-5D to accentuate the image-processing advantage provided by the embodiment of the invention in that the smooth muscle and collagen fiber areas of the tissue otherwise not visually differentiable in the original image are now clearly distinguished in the final image created with the use of the digital staining algorithm. It can be also observed that the visualization of collagen fiber is greatly improved in comparison to the original H&E stained image. A comparison between the pair of digitally-stained images of FIGS. 4D and 5D with that of manually-stained MT images of FIGS. 4B and 5B, respectively, additionally illustrates the reliability of the digital staining procedure in digitally producing colorimetric attributes that are substantially equivalent to those of the manually MT-stained image.

Figure 6:
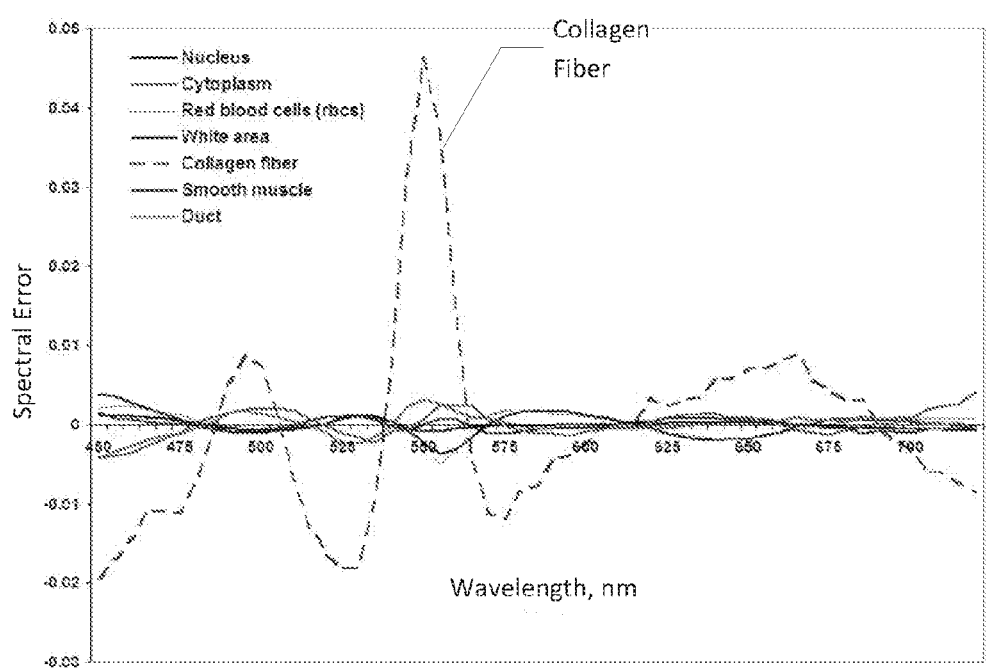
FIG. 6 is a graph of average spectral errors related to different tissue components.
Figure 4:
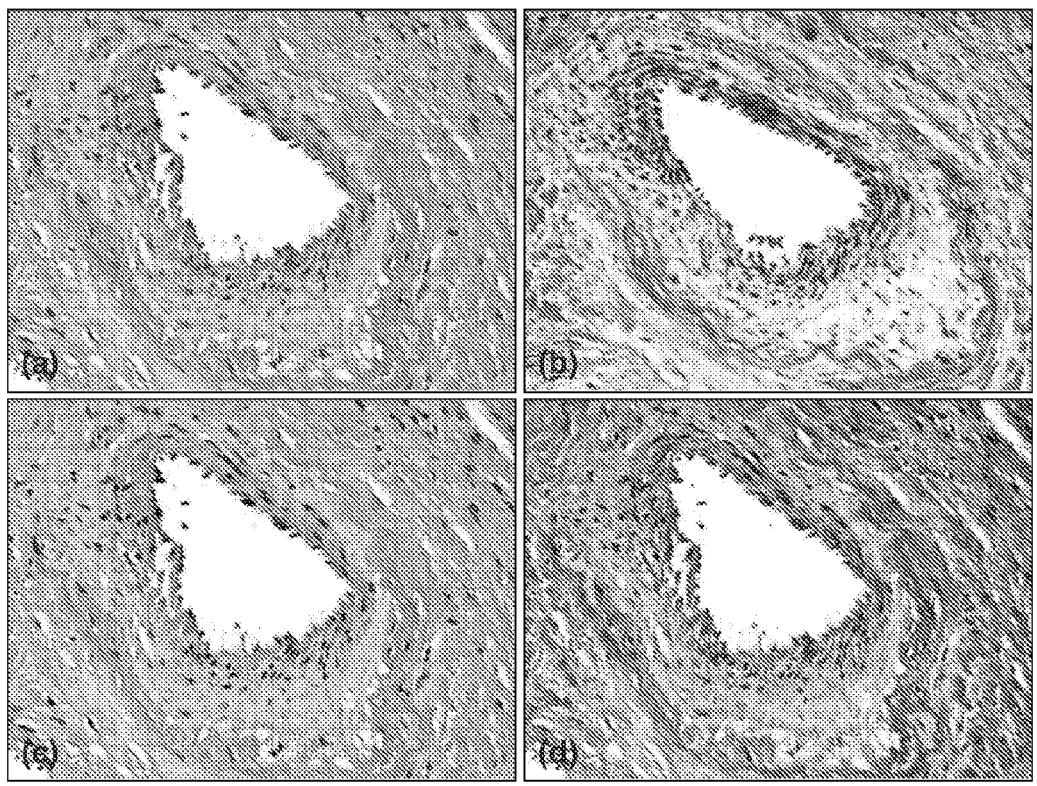
FIGS. 4A-4D are visually-perceivable images obtained at different stages of the process of the invention.
Figure 5:
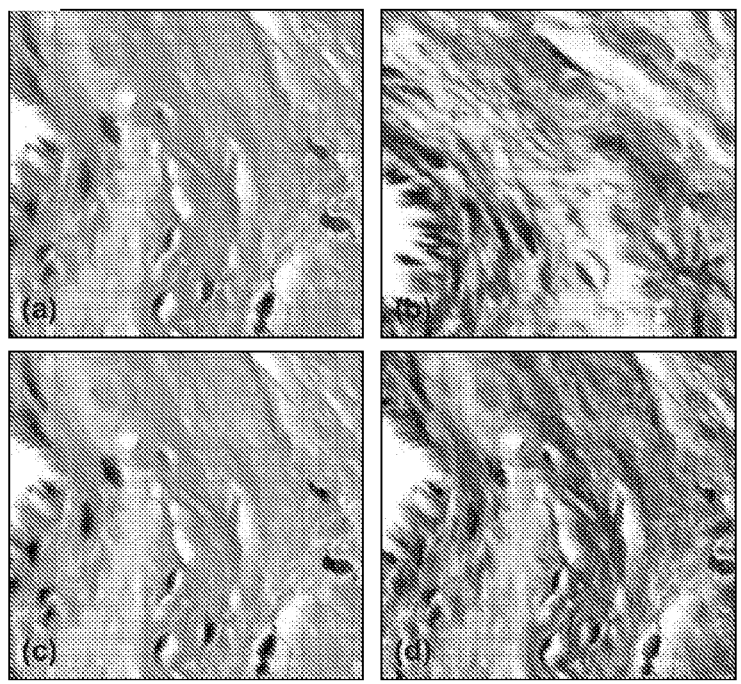
FIGS. 5A-5D show magnified portions of images of FIGS. 4A-4D.
Figure 7:
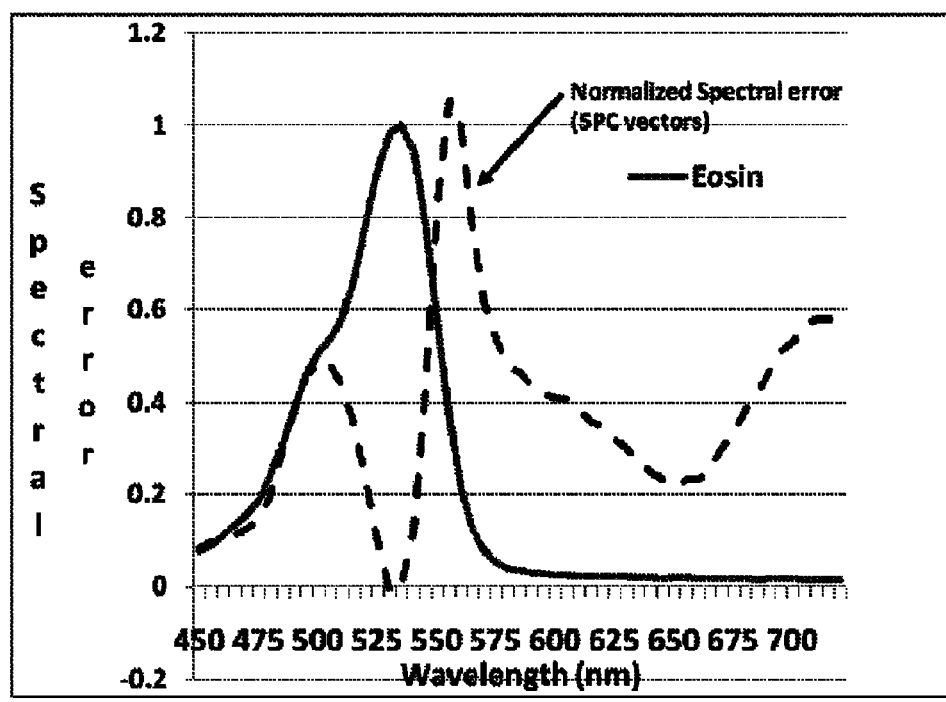
FIG. 7 provides comparison of profiles of the graph of FIG. 6 and that representing absorption spectrum of Eosin dye.

FIG. 6 illustrates the average spectral error calculated for components of the tissue sample analyzed in reference to FIGS. 4 and 5. The presence of noticeable peaks in the spectral error curve for collagen fiber (dashed line) at specific wavelengths demonstrates that results of the modulation, according to an embodiment of the algorithm as described above, of the original spectra of the tissue components are particularly pronounced for the addressed spectra that are intended to be enhanced. A related implementation of the algorithm according to the invention can take advantage of these spectral enhancements features by purposefully designing the weighting matrix W. For example, the algorithm may include an optional step of determining specific wavelength(s) at which the spectral transmission data are further enhanced based on evaluation of the data that represents the spectral error (such as that of FIG. 6). Comparison of data representing the Eosin dye absorption spectrum with the normalized spectral error in FIG. 7 illustrates that similarity of the profiles of these two spectra. This similarity may indicate that the minute difference between the spectra of the collagen fiber and muscle fiber (or any other tissue component) can be explained by their staining reaction to eosin dye.

In accordance with an exemplary embodiment, described with reference to FIGS. 1 and 3, a system and method are provided for imaging a biological tissue and digitally processing of the acquired image in such a way as to mimic the reaction of the tissue to a chosen target stain. While specific values chosen for this embodiment are recited, it is to be understood that, within the scope of the invention, the values of all of parameters may vary over wide ranges to suit different applications. While specific values chosen for these embodiments are recited, it is to be understood that, within the scope of the invention, the values of all of parameters may vary over wide ranges to suit different applications. Modifications and variations of the presented embodiments are also viewed to fall within the scope of the present invention. While described with respect to multispectral images and multispectral imaging systems, it is appreciated that the current method can be applied to other imaging configurations such as, for example, imaging with the use of endoscopy, optical coherence tomography (OCT, optical frequency-domain imaging (OFDI), confocal microscopy, spectrally-modulated full-field optical coherence microscopy for ultrahigh-resolution endoscopic imaging (FFOCM), or image analysis of an appropriate chip hosting identified biological substance such as a circulating tumor cell chip (CTC).

What is claimed is:

1. An apparatus for imaging a biological sample, comprising:
    an input configured to receive at least one of imaging data acquired from and an image of the biological sample; and
    a processor configured to receive the at least one of the imaging data and the image from the input, the image characterized by a first chromaticity parameter and a first transmission spectrum, to enhance spectral signals associated with the at least one of the imaging data and the image to form an enhanced transmission spectrum, and to apply a linear transform to the enhanced transmission spectrum using estimated transmission data and training data to generate a digital representation of a physical reaction of the biological sample to a target chemical stain having a first chemical structure and with which the sample has not been physically stained, said digital representation corresponding to a target image characterized by a second chromaticity parameter that is different from the first chromaticity parameter.

2. An apparatus according to claim 1, wherein at least one of the estimated transmission data and the training data relates to the target chemical stain.

3. An apparatus according to claim 1, wherein:
said biological sample would comprise a first change of an optical characteristic thereof upon being physically stained with the target chemical stain; and
said physical reaction includes a second change of the optical characteristic, said first change being substantially the same as said second change.

4. An apparatus according to claim 1, further comprising
a display operably connected to the processor and configured generate at least one of the image of the biological sample, an enhanced image corresponding to said enhanced transmission spectrum, and said digital representation of the physical reaction of the biological sample to the target chemical stain, and
wherein an enhancement of spectral signals includes mapping the imaging data to scale spectral residual errors between the first transmission spectrum and a second transmission spectrum that has been estimated with the use of a multivariate data-analysis algorithm, which algorithm reduces a number of vectors in a space of the imaging data.

5. An apparatus according to claim 1,
wherein the image of the biological sample includes a multispectral image representing a plurality of spectrally-discrete images acquired at a corresponding plurality of discrete spectral bandwidths, and
wherein the processor is configured to apply said linear transform to generate a digital representation of a physical reaction of the biological sample, which has been physically stained with a chemical stain having a second chemical structure, to the target chemical stain.

6. A method for digital staining of a histopathology image, the method comprising:
receiving an image of a tissue sample that contains colorimetrically-similar tissue components to acquire original spectral transmission data representing said tissue sample;
digitally modifying the original spectral transmission data based on at least one of (i) a numerically estimated reference spectral transmission data and (ii) a modulation factor modulating an original spectral transmission data vector shifted by the estimated reference spectral transmission data vector to derive enhanced spectral transmission data representing spectral differences between the colorimetrically-similar tissue components; and mapping the enhanced spectral transmission data into target spectral transmission data corresponding to a spectral response of said tissue sample to being physically stained with a target stain which has a first chemical structure and with which said tissue sample has not been physically stained.

7. A method according to claim 6, further comprising at least one of converting said target spectral transmission data into an RGB color space and presenting an image corresponding to so converted target spectral transmission data for visualization.

8. A method according to claim 6,
wherein the receiving an image includes receiving an image having a first chromaticity parameter and in which a difference between image portions corresponding to colorimetrically-similar tissue components is not perceivable by an eye of a human and
wherein the mapping includes mapping the enhanced spectral transmission data into target spectral transmission data representing a target image characterized by a second chromaticity parameter that is different from the first chromaticity parameter.

9. A method according to claim 6, wherein the modifying of the original spectral transmission data includes modifying said data based on transmission parameters that are dependent on a spectral characteristic of an image of a background scene against which the tissue sample is imaged.

10. A method according to claim 6, wherein the mapping of the enhanced spectral transmission data includes applying a linear transformation of said data that is defined based on predefined tissue classifications with respect to the target stain.

11. A computer program product for use on a computer system for assigning color-codes to colorimetrically-similar components of a biological tissue, the computer program product comprising:
a tangible non-transitory computer-usable storage medium having computer-readable program code thereon, the computer readable program code including:
program code for deriving, from an original image of the biological tissue obtained with a multi-spectral imaging system and characterized with a first chromaticity parameter, image parameters representing spectral transmission difference between colorimetrically-similar components of the biological tissue; and
program code for color-coding of said image parameters based on reference image data, enhanced image data, and training data such as to digitally generate a target image representing a physical reaction of the biological tissue to a target chemical stain which has a first chemical structure and with which the biological tissue has not been physically stained,
wherein the enhanced image data represent a scaled spectral difference between a first transmission spectrum of the original image and a second transmission spectrum represented by the reference image data,
said colorimetrically-similar components being visually discernable in the target image,
and
wherein the target image is characterized by a second chromaticity parameter that is different from the first chromaticity parameter.

12. A computer program product according to claim 11, wherein color-codes are assigned based on coefficients representing linear relationship between the enhanced image data and the target image.

13. A computer program product according to claim 11, wherein the computer-readable program code further includes program code for storing, on said tangible computer-usable storage medium, a plurality of image data sets correspondingly representing at least said colorimetrically-similar components in a plurality of discrete spectral bands.

14. An apparatus for imaging a biological sample, comprising: an optical system including: an input configured to receive light from the biological sample; an output connected to the input along at least one optical axis; a spectrally-selective system disposed along the at least one optical axis between said input and output and configured to process the light in a plurality of discrete spectral bandwidths to form a plurality of image-forming signals corresponding to said plurality of discrete spectral bandwidths; a detector configured to receive the plurality of image-forming signals corresponding to said plurality of discrete spectral bandwidths and to form a plurality of images therefrom; a processor programmed to: receive an image from the plurality of images, the image characterized by a first chromaticity parameter and having a first transmission spectrum; spectrally enhance the image to produce an enhanced transmission-spectrum image; transform said enhanced transmission-spectrum image to digitally form a target image digitally representing a physical reaction of the biological sample to a potential target chemical stain that has a first chemical structure and with which the biological sample has not been physically stained; and a display configured to display a visually-perceivable representation of said target image illustrating the biological sample having the potential target chemical stain digitally applied to the biological sample, wherein the target image is characterized by a second chromaticity parameter that is different from the first chromaticity parameter.

15. The apparatus according to claim 14, wherein said processor is further programmed to spectrally enhance the image to differentiate between colorimetrically-similar components of the biological sample, said spectral enhancement including mapping of the image to scale spectral residual errors between the first transmission spectrum and a second transmission spectrum that has been estimated with the use of a multivariate data-analysis algorithm, which algorithm reduces a number of vectors in a space of imaging data corresponding to the plurality of images.

16. The apparatus according to claim 14, wherein said transformation of said enhanced transmission-spectrum image includes a linear transformation of said enhanced-transmission spectrum image, the linear transformation being defined as a matrix product of a pseudo-inverse matrix containing estimated transmission data and a matrix containing target transmission data.

17. The apparatus according to claim 16, wherein the target transmission data is derived from a target data set including data corresponding to visually-perceivable properties of the potential target chemical stain applied to a reference biological sample, and wherein said spectral enhancement includes said mapping based on the second transmission spectrum that has been estimated as a sum of
(i) dominant principal component vectors, of the multivariate data-analysis algorithm and
(ii) a spectral transmission vector representing those portions of the image that do not represent colorimetrically-similar components of the sample and that are excluded from being spectrally enhanced.

18. A system for image analysis, the system comprising:
an imaging device generating at least one image of an object, said at least one generated image including image acquisition parameters representing colorimetrically-similar components of the object that are nor visually-distinguishable, said at least one generated image characterized by a first chromaticity parameter and having a first transmission spectrum; and
a calibration device operably connected to the imaging device and adapted to receive the at least one generated image and to change at least one image acquisition parameter based on a digital comparison between
(i) the image acquisition parameters included in said at least one generated image and
(ii) target image acquisition parameters that would be acquired by said colorimetrically-similar components in response to exposure of the object to a target chemical reaction with a target chemical stain to which the object has not been physically exposed,
wherein said target chemical stain has a first chemical structure, and
wherein said target image acquisition parameters correspond to a target image characterized by a second chromaticity parameter that is different from the first chromaticity parameter.

19. A system according to claim 18, wherein the at least one generated image represent the object physically stained with a chemical stain having a second chemical structure that is different from the first chemical structure, and wherein the target chemical reaction includes staining the colorimetrically-similar components with the target chemical stain.

20. A system according to claim 18, wherein the changing of at least one image acquisition parameter includes changing said parameter based on a combination including said parameter, a reference spectral transmission data obtained in the process of generating the at least one image, and a linear scaling factor.

21. A system according to claim 20, wherein said linear scaling factor depends on an estimated image acquisition parameter representing a response of colorimetrically-similar components to a target chemical reaction.

22. A system according to claim 18, wherein the calibration device includes a computer processor programmed to derive the at least one image acquisition parameter from the at least one image generated by the imaging device, and wherein the imaging device is configured to produce images of the object in discrete spectral bands.

23. A system according to claim 18, wherein the calibration device is further adapted to change at least one image acquisition parameter by scaling spectral differences between the first transmission spectrum and a second transmission spectrum that has been estimated with the use of a multivariate data-analysis algorithm that reduces a number of vectors in a space of imaging data.

24. An apparatus according to claim 4,
wherein the enhancement of spectral signals includes said mapping based on the second transmission spectrum that has been estimated as a sum of
(i) dominant principal component vectors, of the multivariate data-analysis algorithm and
(ii) a spectral transmission vector representing those portions of the image that do not represent colorimetrically-similar components of the sample and that are excluded from being spectrally enhanced.

25. A computer program product according to claim 11, wherein the reference image data are estimated with the use of dominant principal component vectors of a multivariate data-analysis algorithm that reduces a number of vectors in original spectral transmission data corresponding to the original image.

* * * * *